SELECTIVE CONVERSION OF NORMAL PARAFFINS

Original Filed June 13, 1958 3 Sheets-Sheet 1

Jackson Eng
Roger M. Butler Inventors

By

Reuben Wilder Patent Agent

EFFECT OF CONTACTING TEMPERATURE
UPON POUR POINT REDUCTION

Jackson Eng
Roger M. Butler Inventors

By

Patent Agent

EFFECT OF CONTACTING TEMPERATURE UPON SIEVE CAPACITY

0° F. POUR POINT PRODUCT ADJUSTED TO 575° F. INITIAL BOILING POINT

Jackson Eng
Roger M. Butler Inventors

By

Patent Agent

United States Patent Office

Re. 28,300
Reissued Jan. 14, 1975

28,300
SELECTIVE CONVERSION OF NORMAL PARAFFINS

Roger M. Butler and Jackson Eng, Sarnia, Ontario, Canada, assignors to Esso Research and Engineering Company Original No. 3,294,858, dated Dec. 27, 1966, Ser. No. 267,376, Feb. 28, 1963, which is a division of application Ser. No. 741,906, June 13, 1958. Application for reissue Oct. 16, 1972, Ser. No. 297,760, which is a continuation of abandoned reissue application Ser. No. 793,207, Dec. 26, 1968

Int. Cl. C07c *3/34*

U.S. Cl. 260—683 R 5 Claims

Matter enclosed in heavy brackets [ ] appears in the original patent but forms no part of this reissue specification; matter printed in italics indicates the additions made by reissue.

*ABSTRACT OF THE DISCLOSURE*

*Normal paraffins contained in hydrocarbon fractions boiling between 100° and 750° F. are selectively converted by contact over a crystalline metallic alumino-silicate having uniform pore spaces of about 5 angstrom units at a temperature of about 800 to 1000° F. with a gas selected from the group consisting of hydrogen, nitrogen, carbon dioxide and inert gas.*

*This is a continuation of application Ser. No. 793,207, filed Dec. 26, 1968, now abandoned.*

*Cross References to Related Applications*

This application is a divisional application of Serial No. 741,906, filed June 13, 1958.

The present invention relates to the upgrading of hydrocarbon oils and more particularly relates to an improved process for eliminating normal paraffin hydrocarbons from oils in which they are present in admixture with other hydrocarbons which comprises contacting such oils with a metallic alumino-silicate having uniform pore spaces of about 5 Angstrom units under conditions such that normal paraffins are continuously adsorbed into the alumino-silicate and continuously converted to olefins which are recovered with the non-adsorbed constituents of the oil.

The invention in a preferred embodiment is a process for lowering the pour point of a middle distillate, boiling between 300° and 650° F., by treating it in the vapor phase with a 5 A. alumino-silicate at a temperature between 800° and 900° F. and at a space velocity of 0.3 to 1.2 lb./lb., removing any by-product boiling below 300° F. and recondensing the vaporized product.

Because of their low octane value in gasolines and their adverse effect upon the pour point and cloud point of hydrocarbon oils generally, normal paraffins are undesirable in high octane gasolines, aviation turbo-jet fuels, kerosines, heating oils, lubricating oils and other premium quality petroleum products. Recognition of this fact has spurred efforts to develop processes which will permit the removal of normal paraffins from oils intended for use in the manufacture of such products. One of the most promising methods proposed for separating normal paraffins from branched chain and cyclic compounds developed to date involves the use of adsorbents which are selective for the normal paraffin molecules. These adsorbents, generally referred to as molecular sieves, are crystalline metallic alumino-silicates containing a large number of submicroscopic cavities interconnected by many smaller pores or channels which are extremely uniform in size. Molecules having affinity for the alumino-silicate and small enough to enter the pores or channels are readily adsorbed, while those of greater size or lacking such affinity are rejected. By employing alumino-silicates having uniform pore spaces of about 5 Angstrom units in diameter, excellent separations between normal paraffins and other hydrocarbons present in hydrocarbon oils can be made.

The scientific and patent literature contains numerous references to the composition and adsorbing action of metallic alumino-silicates. In general these are crystalline zeolite containing an alkali or alkaline earth metal, aluminum, silicon and oxygen. They may be either natural or synthetic in origin and may have uniform pore spaces of from about 3 to about 15 Angstrom units, depending upon their composition and the conditions under which they were formed. As mentioned above, those having pores of about 5 Angstroms are useful for separating normal paraffins from branched chain and cyclic compounds. Among the natural zeolites having molecular sieve properties may be mentioned analcite, $$NaAlSi_2O_6 \cdot H_2O$$

and chabasite, $CaAl_2Si_4O_{12} \cdot 6H_2O$. Synthetic zeolites having similar properties are described in U.S. Patent No. 2,306,610, where a material of the formula $$(CaNa_2)\ Al_2Si_4O_{12} \cdot 2H_2O$$

is set forth, and in U.S. Patent No. 2,522,426, which discloses a composition having the formula $$4CaO \cdot Al_2O_3 \cdot 4SiO_2$$

Other molecular sieves are described in articles by Brack and others which were published in the Journal of the American Chemical Society, volume 78, page 693 et seq. in December 1956.

Despite the excellent selective adsorption properties of molecular sieves, certain difficulties have been encountered in attempting to apply them to the large scale removal of normal paraffin hydrocarbons from branched chain and cyclic hydrocarbons. In using such adsorbents, it is necessary to employ a two-step cyclic process. The normal paraffins must first be selectively adsorbed upon the molecular sieve. Usually this is accomplished by contacting the oils with the adsorbent at temperatures in the range of from about 100° to about 600° F. and at pressures of from about atmospheric to about 100 p.s.i.g. Following this adsorption step, the molecular sieve must next be reactivated by a desorption step before it can be used for adsorption again. The desorption step is usually carried out by steaming the used adsorbent, evacuating it, or displacing the adsorbed compounds by means of a gas which is not itself adsorbed by the sieve. The capacity of molecular sieve adsorbents when used in this manner is very low and therefore such cyclic processes are relatively expensive because of the frequency with which the sieve must be desorbed. The desorption methods available are only partially effective and the selectivity and capacity of the sieve rapidly decline as it is used. A further difficulty is that carbonaceous deposits rapidly build up on the surface of the sieve. Regeneration of the sieve at frequent intervals by heating it to very high temperatures or by employing other regenerative techniques allieviates this latter difficulty to some extent but very frequent regeneration shortens the active life of the sieve. Because of these difficulties, the cost of effecting separations between hydrocarbons by means of molecular sieves is inordinately high.

The present invention provides a new and improved method for eliminating normal paraffins from hydrocarbon oils by means of molecular sieves which is free from many of the disadvantages associated with molecular sieve processes employed in the past. The process differs from prior processes in that molecular sieves are employed to effect chemical conversion of the normal paraffins upon a selective basis, rather than merely a mechanical separaion. It has been found that normal paraffins present in hydrocarbon oil can be selectively converted to olefins y contacting the oil with a molecular sieve having pore iameters of about 5 A. under critical conditions. It is elieved that the explanation for this selective conversion henomenon lies in the fact that gas phase configurations are not possible in the pores of molecular sieves. It s impossible for a normal paraffin molecule to rotate in he 5 Angstrom pores of a molecular sieve except on its ongitudinal axis and therefore the rotations corresponding to the three main moments of inertia of the molecule ecome vibrations as the molecule is occluded in the sieve. This results in a high loss in energy of the molecule over n extremely short period of time. By providing the nolecule with a sufficiently high initial energy, it is possible to use this energy loss to effect rupture of bonds in he molecule and convert the normal paraffins into lower nolecular weight olefins before complete occlusion takes place. The olefins are not retained by the sieve but instead are recovered with the non-adsorbed isoparaffins and cyclic compounds in the oil.

Regardless of the theoretical explanation for the phenomenon which takes place, the process of the invention has numerous advantages over processes which have been proposed for the removal of normal paraffins from hydrocarbon oils by means of molecular sieves in the past. Since the normal paraffins which would otherwise be occluded by the sieve are continuously converted to olefins which are not retained on the sieve, the pores of the sieve remain relatively free of hydrocarbons. No desorption step is necessary and the difficulties encountered in desorbing the sieve in prior processes are thus avoided. Olefins formed in the process can readily be separated from saturated constituents in the oil and form a valuable by-product. The simplified procedure and equipment employed make the process considerably more attractive from an economic standpoint than processes utilized heretofore.

Molecular sieve adsorbents suitable for use in the process of the invention are available commercially and may be produced in a number of ways. One suitable process for preparing such adsorbents involves the mixing of sodium silicate, preferably sodium metasilicate, with sodium aluminate under carefully controlled conditions. The sodium silicate employed should be one having a ratio of soda to silica between about 0.8 to 1 and about 2 to 1. Water glass and other sodium silicate solutions having lower soda to silica ratios do not produce the selective adsorbent crystals unless they are subjected to extended heat soaking or crystallization periods. Sodium aluminate solutions having a ratio of soda to alumina in the range of from about 1 to 1 to about 3 to 1 may be employed. High soda to alumina ratios are preferred and sodium aluminate solutions having soda to alumina ratios of about 1.5 to 1 have been found to be eminently satisfactory. The amounts of the sodium silicate and sodium aluminate solutions employed should be such that the ratio of silica to alumina in the final mixture ranges from about 0.8 to 1 to about 3 to 1 and preferably from about 1 to 1 to about 2 to 1.

These reactants are mixed in a manner to produce a precipitate having a uniform composition. A preferred method for combining them is to add the aluminate to the silicate at ambient temperatures using rapid and efficient agitation to produce a homogeneous mixture. The mixture is then heated to a temperature of from about 180° to about 215° F. and held at that temperature for a period of from about 0.5 to about 3 hours or longer. The crystals may be formed at lower temperatures but in that case longer reaction periods are required. At temperatures above about 250° F. a crystalline composition having the requisite uniform size pore openings is not obtained. During the crystallization step, the pH of the solution should be maintained on the alkaline side at about 12 or higher. At lower pH levels, crystals having the desired properties are not as readily formed.

The crystals prepared as described above have pore diameters of about 4 Angstrom units. To convert these to crystals having 5 Angstrom pores, it is necessary to employ a base exchange reaction for the replacement of some of the sodium by calcium, magnesium, cobalt, nickel, iron or a similar metal. Magnesium, cobalt, nickel and iron have greater cracking activity than does calcium and therefore it will often be preferred to employ solutions of these metals for replacement purposes.

The base exchange reaction may be carried out by water washing the sodium alumino-silicate crystals and adding them to a solution containing the desired replacement ions. An aqueous solution of magnesium chloride of about 20% concentration, for example, may be used for preparation of the magnesium form of the 5 Angstrom sieve. After a contact time which may range from about 5 minutes to about an hour, the 5 Angstrom product is filtered from solution and washed free of the exchange liquid. About 50 to 75% of the sodium in the crystals is normally replaced during the base exchange reaction.

The crystals thus prepared are in a finely divided state and are usually pelleted with a suitable binder material before they are calcined in order to activate them. Any of a number of binder agents used in the manufacture of catalysts may be employed for this purpose. A binder consisting of bentonite, sodium silicate and water, for example, has been found satisfactory. In using this binder, the constituents should be mixed so that the product contains from about 5 to 10% bentonite, 5 to 15% sodium silicate and about 75 to 90% of the crystals on a dry basis and that the total mixture contains about 25 to 35% water. This mixture may then be extruded into pellets or otherwise shaped and subsequently dried and calcined. Calcination temperatures of from about 700° to about 900° F. or higher are satisfactory.

In carrying out the process of the invention, the feed stream is contacted with the molecular sieve adsorbent in vapor phase at a temperature of from about 800° to about 1000° F. At temperatures below about 800° F. little conversion takes place and therefore removal of normal paraffins from the oil is low. At temperatures above about 1000° F. considerable thermal cracking of isoparaffinic and cyclic constituents of the oil takes place and hence much of the selectivity of the process disappears. Contacting temperatures of from about 800° to 900° F. are most effective and a temperature of about 850° F. is particularly preferred.

The pressures employed in contacting the oil with the adsorbent may range from about 50 mm. of mercury to about 150 p.s.i. Generally it is preferable to carry out the contacting step at about atmospheric pressure. The feed rate employed may range from about 0.1 to about 3 pounds of oil per pound of molecular sieve per hour. Preferred rates range between 0.1 and 1.0 pounds per pound per hour. Under these conditions, normal paraffins present in the oil will be selectively converted to lower boiling olefins which are not retained upon the sieve and instead are discharged with the product oil. These olefins may be readily separated from the oil and constitute a valuable by-product of the process.

Although the olefins formed by the selective conversion of normal paraffins in the process are not retained upon the sieve, deposits gradually build up on the sieve surface, probably due to polymerization of the olefins. Sulfur compounds, water and other contaminating materials present in the feed may also contribute to the gradual accumulation of such deposits. In order to remove these deposits and maintain the activity of the adsorbent at a high level, the sieve is regenerated at suitable intervals. Although steam and other regeneration procedures heretofore disclosed may be employed in this step of the process, it is normally preferred to regenerate the sieve by passing a stream of oxygen-containing gas through the sieve bed at high temperatures. In the presence of the oxygen, the deposits are burned from the surface of the sieve and the sieve activity is restored. The quantity of oxygen required for this burning step is small, since the total amount of foreign matter on the sieve is small, and therefore gas streams containing as little as 5% oxygen may be used. It is preferred, however, to employ air for this purpose. The air or other gas stream used in the regenerative step may be preheated to a temperature of from about 500° to about 800° F. before contacting it with the sieve. The high temperature zone formed by combustion of the deposits upon the sieve surface proceeds through the adsorbent mass rapidly and exists at any one spot for only a brief instant. It has been found that the sieve crystals are not appreciably impaired by this regenerative treatment.

In order to further minimize deposit formation and reduce the frequency of regeneration, it is often advantageous to contact the feed stream with a guard bed of alumina, silica gel or a similar adsorbent prior to introducing it into the treating zone. Polar contaminants in the feed are removed by the guard bed and hence the formation of deposits within the treating zone is reduced. The guard bed may be regenerated by burning or other conventional techniques.

In order to further reduce deposit formation within the treating zone, it is preferred to carry out the process in the presence of added hydrogen, nitrogen, carbon dioxide or a similar gas having a molecular diameter smaller than the pore diameter of the sieve. The presence of such a gas serves to purge hydrocarbon fragments from the pores of the molecular sieve and prevent the reaction of such fragments to form carbon and polymeric deposits. Hydrogen is particularly preferred for this purpose because it may also result in saturation of some of the olefins produced and thus further reduce deposit formation. The use of hydrogen is particularly effective in the presence of metallic alumino-silicate adsorbents which have some hydrogenation properties. The nickel form of 5 A. molecular sieve, for example, tends to cause hydrogenation of the olefin to a greater degree than does the calcium form and therefore deposit formation is reduced. The gas employed may be introduced with the feed at a rate such that its concentration in the reactor ranges from about 5 to about 95 mole percent.

The oils adapted for treatment in accordance with the process of the invention may in general be defined as hydrocarbon oils boiling in the range between about 100° to about 750° F. and especially between 320° and 650° F. Such oils include naphthas, kerosine (boiling between 320° and 550° F.) and middle distillates and are widely used for the production of gasolines, jet fuels, diesel fuels, heating oils and similar products wherein the content of normal paraffins must be limited to control undesirable effects such as solidification in storage at low temperature. The process of the invention is particularly effective for removing wax and similar normal paraffinic constituents from middle distillate petroleum fuels in order to reduce their pour point, cloud point and haze point, and it is in this area that the process of the invention will find widest application.

The exact nature and objects of the invention may be more readily understood by referring to the following detailed description of a preferred embodiment of the process, to the examples set forth hereafter, and to the attached drawings in which.

Figure 1:
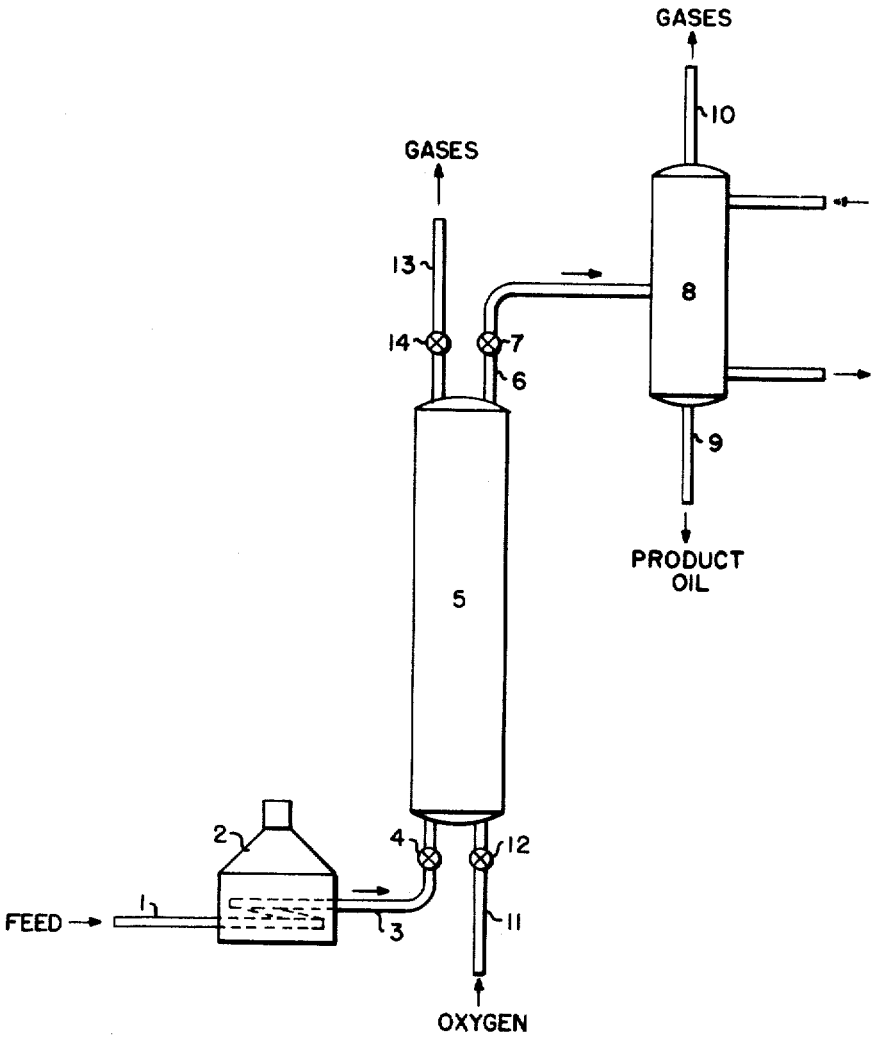
FIG. 1 depicts a flow diagram of a preferred embodiment of the process of the invention.

Referring now to FIGURE 1 a hydrocarbon oil containing normal paraffins as well as iso-paraffinic and cyclic compounds, a gas oil boiling in the range of from about 450° to about 700° F., for example, is introduced through line 1 into furnace 2 where it is preheated to a temperature of about 850° F. The preheated feed, now in vapor phase, is passed through line 3 and 4 into contacting zone 5. Hydrogen or a similar gas having a molecular diameter less than 5 Angstrom units may be introduced with the vaporized feed into zone 5. The contacting zone has disposed therein a bed of molecular sieve having uniform pore diameters of 5 Angstrom units. The contacting zone may be fitted with suitable jacketing, heat coils or similar means for controlling temperature within the bed. The feed stream passes upwardly through the adsorbent bed and in so doing, normal paraffins present therein are selectively converted to lower molecular weight olefins. Some light gases are also formed. The vapor stream after contact with the absorbent is removed overhead from contacting zone 5 through line 6 containing valve 7 and is passed to condenser 8. In the condenser, hydrocarbons boiling above about 100° F. are condensed and taken off as a bottoms product through line 9. Uncondensed gases are removed overhead through line 10. The product oil recovered through line 9 may be further fractionated to remove constituents boiling below the feed boiling point if desired. The overhead gas stream may be passd to a light ends plant for separation and recovery of the individual gaseous constituents.

The contacting procedure described above is continued until the concentration of normal paraffins in the product stream withdrawn through line 9 reaches an unacceptable level. This concentration may readily be determined by ultra violet analysis, infra red analysis, refractive index determination or the like. At this point sufficient deposits have formed upon the sieve surface to require regeneration of the sieve. Introduction of the feed stream is therefore halted and following nitrogen or other inert gas, air or other oxygen containing gas is introduced into the bottom of contacting zone 5 through line 11 containing valve 12. The gas stream should be preheated to a temperature of from about 500° to 800° F. This may be accomplished in a suitable furnace, not shown. Under the temperature conditions prevailing within the sieve bed, oxygen in the gas stream combines with the deposits on the sieve surface and the deposits are burned off. The combustion takes place within a narrow zone which moves from the bottom of the bed to the top of the bed. At any instant the temperature within the combustion zone may range from 1000° to 1500° F, but because of the short time during which these temperatures prevail at any level in the bed, crystallinity of the sieve is not materially affected. Gases are removed overhead from the contacting zone through line 13 containing valve 14. Upon completion of the regenerating step of the process, valves 12 and 14 may be closed and valves 4 and 7 opened to permit resumption of the contacting step. Although only one contacting vessel is shown in FIGURE 1, it will be understood that in most cases it will be advantageous to employ two or more vessels suitably connected in parallel to permit regeneration of the spent sieve without interruption of the process. The arrangement of such vessels will be obvious to those skilled in the art.

The process of the invention is further illustrated by the following examples.

EXAMPLE 1

A petroleum middle distillate boiling between about 326° F. and about 680° F. was contacted with a calcium form molecular sieve having uniform pore diameters of 5 Angstrom units by passing the feed stream downflow through a fixed bed containing 500 grams of the sieve. The contacting temperature was 850° F. and the pressure was about 760 mm. of mercury. The feed rate averaged 1 pound of oil per pound of sieve per hour. This contacting was continued until about 750 grams of the oil had been passed through the sieve bed. At this point the operation was discontinued and the product collected was analyzed. A similar run was then made in which the feed stream was contacted with the sieve at a temperature of 390° F. and at a pressure of 0.2 mm. of mercury. Again the product recovered from the contacting zone was collected and analyzed. Inspections of the feed stream and the products from these two operations are shown in Table I below.

Table I

INSPECTION OF FEED AND PRODUCTS

| ASTM D-158 Distillation | Feed | 850° F. Product | 390° F. Product |
|---|---|---|---|
| I.B.P. | 326 | 108 | 328 |
| 5% | 369 | 180 | 362 |
| 10% | 385 | 320 | 378 |
| 20% | 415 | 352 | 406 |
| 30% | 440 | 418 | 430 |
| 40% | 472 | 456 | 456 |
| 50% | 504 | 502 | 488 |
| 60% | 533 | 534 | 520 |
| 70% | 562 | 560 | 552 |
| 80% | 592 | 579 | 584 |
| 90% | 623 | 592 | 620 |
| 95% | 642 | 598 | 654 |
| F.B.P. | 680 | 652 | 676 |
| Pour Point, ° F | +5 | * −55 | −40 |
| Cloud Point, ° F | +16 | * −55 | −32 |
| R.I. at 20° C | 1.4630 | * 1.4737 | 1.4662 |
| Bromine No. | 0.4 | 17.1 | 0.5 |

* 850° F. product adjusted to 325° F. initial boiling point.

From the distillation data set forth in the above table it can be seen that an appreciable quantity of low boiling material was formed in the run carried out at 850° F., while essentially none was formed during the low temperature run. The initial 10% of the product collected in the 850° F. run had an extremely high bromine number, indicating that this fraction consisted largely of olefins. The pour point and cloud point data found in the table show that normal paraffins present in the feed stream were reduced to a much greater extent in the high temperature run than in the 390° F. run. This was true even after material boiling below 3250 F. was removed from the 850° F. product. In the low temperature run it was found that the sieve bed rapidly became saturated with normal paraffins. In the high temperature run the sieve was inspected at the end of the run and there was no evidence of any hydrocarbons on the sieve. It therefore appears that normal paraffins present in the feed stream were adsorbed upon the sieve in both runs but that in the high temperature run the adsorbed compounds were continuously selectively converted to olefins which were not retained by the sieve.

EXAMPLE 2

A mixed blend gas oil boiling between 575° and 658° F. was passed through a bed containing 850 grams of a 5 A. calcium molecular sieve at temperatures of from 500° to about 1000° F. Data collected in these runs are shown in Table II below.

TABLE II

PRODUCT DISTRIBUTION AT SIEVE SATURATION [1]

| Contracting temp., ° F | 600 | 755 | 850 | 900 | 1,010 |
|---|---|---|---|---|---|
| Pressure, mm. Hg | | | 750 | | |
| Rate, W./w./Hr. | | | 0.5 | | |
| Feed treated, g/100 g. sieves | 83 | 80 | 195 | 190 | 190 |
| Total product, g./100 g. sieves | 70 | 70 | 170 | 158 | 118 |
| Wt. precent on feed | 84.0 | 86.0 | 85.7 | 83.4 | 61.9 |
| Material retained on sieve, g./100 g. sieves | | 7.3 | 7.8 | 7.6 | 10.6 |
| Product distribution, wt. percent on feed: | | | | | |
| Gas ($C_4$ and lighter) | Nil | <0.5 | 5.4 | 6.1 | 15.6 |
| Naphtha ($C_5$ 325° F.V.T.) | Nil | ≈1.0 | 1.9 | 6.3 | 7.3 |
| Product (325–575° F.V.T.) | Nil | 12.0 | 23.7 | 29.3 | 27.5 |
| (575° F.+) | 84.0 | 75.0 | 62.0 | 54.1 | 34.4 |
| Material retained on sieves | | 9.1 | 4.0 | 4.0 | 5.6 |
| Material balance | | 97.6 | 97.0 | 99.8 | [2] 90.4 |

[1] Sieves were considered saturated when products boiling above 55° F. showed no improvement in pour point compared to fresh feed.
[2] Poor material balance believed to be caused by loss of gas.

In order to differentiate between the benefits due to selective conversion of normal paraffins and benefits which might be due to cracking, only material boiling above 575° F. was considered in determining the saturation or exhaustion point. The data show that the amount of feed which can be treated before saturation occurs is considerably greater at temperatures of 850° F. and higher. A temperature of 850° F. showed the most favorable results. At that temperature the total product yield was about 86%, based on the feed. With increasing temperatures, this value decreased appreciably with a corresponding increase in the production of gases. This indicates that a non-selective cracking occurs when too high a temperature is used. Material retained on the sieve at a temperature of 1010° F. was greater than that retained at any of the lower temperatures. This again appeared due largely to non-selective cracking but may also be attributable to increased polymerization of olefins at the higher temperature.

EXAMPLE 3

The product obtained in the runs described in the previous example were analyzed and their inspections are set forth in Table III below.

The inspections in the above table show that the bromine number of the product increased with increases in contacting temperature. The change in bromine number with a change in contacting temperature of from 755° to 900° F. was not appreciable. Increasing the temperature to 1010° F., however, brought about a large increase in bromine number. This indicates that at the lower temperatures, the process was largely limited to selective conversion of the normal paraffins and that at the higher temperature non-selective cracking was taking place.

TABLE III

PRODUCT INSPECTIONS

Mixed Blend Gas Oil Treated with 5 A. Molecular Sieves

| Contacting temp. ° F | | 600 | 765 | 850 | 900 | 1,010 |
|---|---|---|---|---|---|---|
| Liquid product: | | | | | | |
| Bromine No. | 2 | 4 | 6 | 6 | 7 | 11 |
| Mercaptan No. | 4.2 | 0.5 | 0.4 | Nil | 0.2 | 0.1 |
| Total S. wt. percent | 0.42 | 0.44 | 0.44 | 0.40 | 0.48 | 0.51 |
| Visc. 100° F. SUS | 47.6 | 47.0 | 45.2 | | 46.0 | 41.2 |
| Aniline pt., ° F | 172 | | | 156 | | |
| R.I. at 68° F | 1.4778 | 1.4813 | | 1.4855 | | |
| Percent gas on feed | | Nil | <0.15 | 5.4 | 6.1 | 15.6 |
| Total gas: | | | | | | |
| Hydrogen, mol. Percent | | (*) | | 21.7 | | 22.8 |
| Methane | | (*) | | 11.3 | | 29.0 |
| Ethylene | | (*) | | | 6.1 | 9.8 |
| Ethane | | (*) | | | 15.2 | 17.5 |
| Propylene | | (*) | | | 22.1 | 15.7 |
| Propane | | (*) | | | 14.4 | |
| Butene-1 | | (*) | | | 2.5 | |
| Butene-2 | | (*) | | | 2.9 | 5.2 |
| Isobutene | | (*) | | | 1.5 | |
| n-Butane | | (*) | | | 2.3 | |
| Gas gravity | | (*) | | | 1.01 | 0.79 |

*Essentially no gas produced.

EXAMPLE 4

Figure 2:
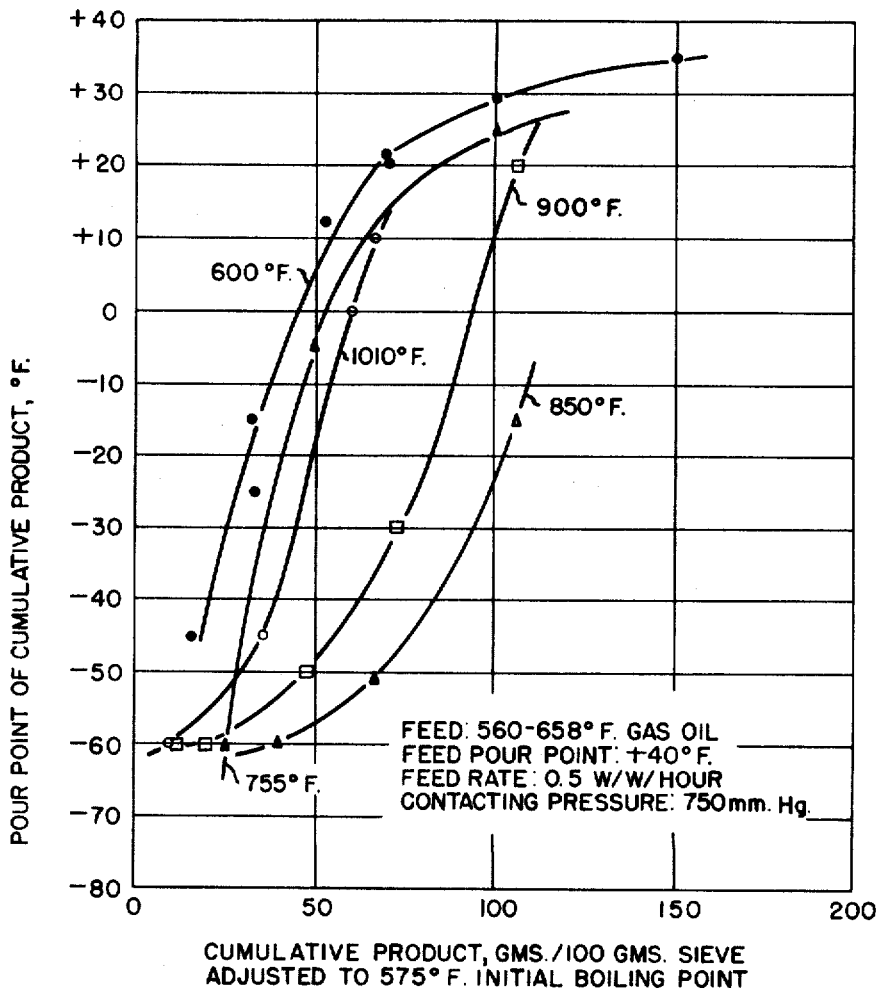
FIG. 2 is a graphical representation of data showing the effect of contacting temperature upon the reduction in pour point of a gas oil treated in accordance with the invention.

Samples of the product obtained at intervals during the runs described in Example 2 were tested to determine their pour points. These samples had been "flashed" to an initial boiling point of 575° F., approximately the initial boiling point of the feed, in order to avoid distortion of the results that would otherwise have been caused by the presence of the low boiling cracked materials, which naturally have low pour points. These pour point data are shown in FIGURE 2 of the drawing. From the figure it can be seen that greater quantities of considerably lower pour point product can be obtained by contacting the feed at temperatures of 850° to 900° F. than can be obtained by treating the feed at higher or lower temperatures. At the lower temperatures the sieve rapidly becomes saturated and little further improvement in pour point results. At high temperatures above about 1000° F. non-selective cracking takes place and the pour point is not improved as much.

EXAMPLE 5

Figure 3:
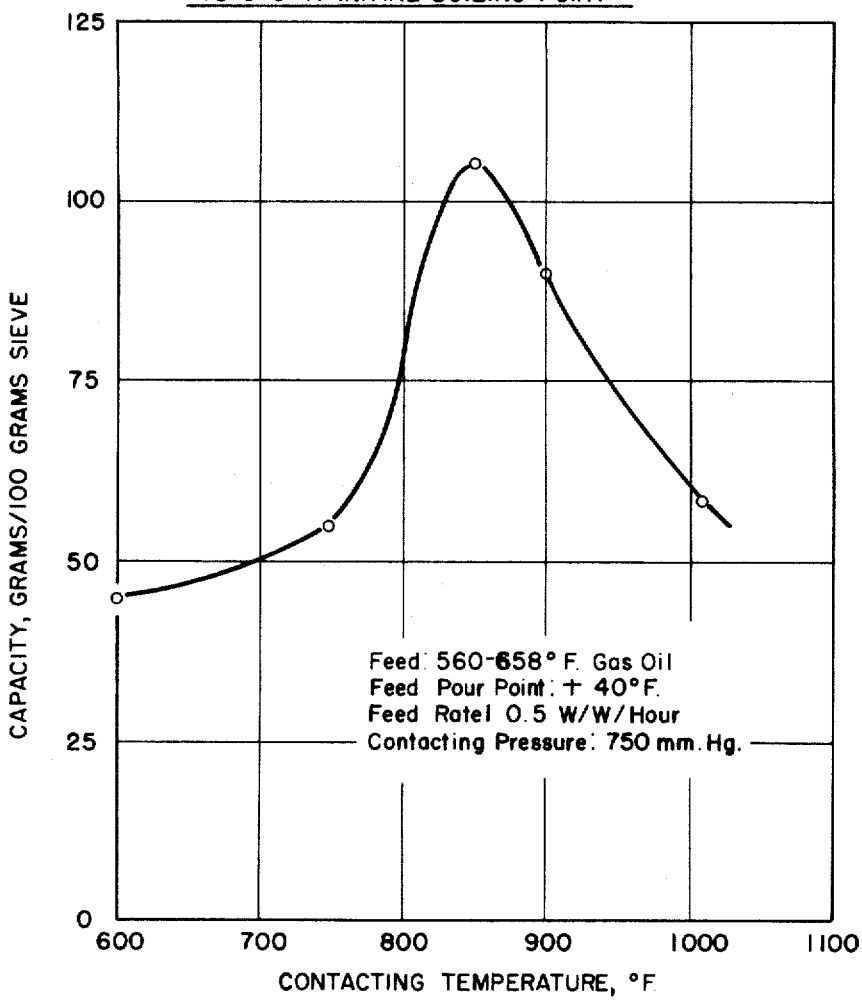
FIGURE 3 is a graphical representation of data illustrating the effect of contacting temperature upon sieve capacity in the treatment of a gas oil in accordance with the invention.

Based on data obtained in the runs set forth in Example 2, sieve capacity as various temperatures for a 0° F. pour point product was determined. The results of these determinations are shown in FIGURE 3. The data thus presented illustrate the critical effect of the contacting temperature upon sieve capacity. At a temperature of about 850° F. capacities in excess of 100 grams per 100 grams of sieve are obtained. At temperatures higher than 950° F., or lower than 800° F., capacity rapidly falls off.

EXAMPLE 6

In order to determine the effect of contacting pressure upon the selective conversion of normal paraffins, a gas oil was contacted with a 5 A. molecular sieve at a temperature of 980° F. and 750° mm. of mercury. A sample of the same gas oil was then tested under similar conditions except that the pressure was reduced to 200 mm. of mercury. It was found that the reduction in pressure improved the selective conversion of normal paraffins somewhat. This improvement, however, did not increase the yield of accumulative product in excess of that obtained at 850° F. and 750 mm. of mercury. Operation under the latter conditions is therefore to be preferred.

EXAMPLE 7

A number of runs were also conducted at a feed rate of 1.5 w./w./hr. and the results obtained were compared with those obtained in earlier runs carried out at 0.5 w./w./hr. It was found that increasing the feed rate from 0.5 to 1.5 w./w./hr. without changing the temperature gave a lower yield of good product. By increasing the temperature to 950° F., however, it was possible to operate at the higher feed rate without any significant reduction in sieve capacity over that obtained at 850° F. with the lower feed rate.

EXAMPLE 8

In order to further demonstrate the effect of temperature and pressure upon the process of the invention, a $C_6$ naphtha was processed with a 5 A. molecular sieve at a temperature of 1100° F. and a pressure of 100 p.s.i.g. The feed rate was 1 v./v./hr. At this temperature and pressure it was found that a substantial amount of the naphtha was thermally cracked to form low boiling gases. Despite this thermal cracking, however, a considerable amount of selective conversion, nevertheless, took place as shown by the following data.

TABLE IV

TREATMENT OF $C^6$ NAPHTHA 1,100° F., 100 p.s.i.g.

| Liquid product components, vol. percent | Feed | Product |
|---|---|---|
| n-Hexane | 52.3 | 36.1 |
| $C_6$ isoparaffins | 30.4 | 30.3 |
| $C_6$ naphthenes | 11.3 | 9.0 |
| Other type hydrocarbons | 6.0 | 24.6 |
| Ratio n-hexane to Isop. plus naphthenes | 1.25 | 0.92 |

From the above table it can be seen that the ratio of normal hexane to isoparaffins and naphthenes decreased from 1.25 to 0.92, indicating that normal paraffins were converted in the presence of the molecular sieve, in preference to isoparaffins and naphthenes. Under the conditions which have been found necessary for carrying out the process of the invention, thermal cracking does not occur to a significant extent and therefore the improvement in the ratio of straight chain compounds to isoparaffins and naphthenes would be considerably higher.

EXAMPLE 9

Samples of a mixed blend heavy atmospheric gas oil having an ASTM boiling range between 560 and 658° F. and a pour point of +40° F. were contacted with a 5 A. molecular sieve in the presence and in the absence of added hydrogen in order to demonstrate the effect of a gas having a molecular diameter less than that of the sieve upon the process of the invention. The contacting temperature employed was 850° F. Pressure within the contacting zone was held at 750 mm. of mercury. The feed rate in both cases was 0.1 pound of feed per pound of sieve per hour. In the first run no hydrogen was used and in the second hydrogen was introduced with the feed at a rate such that the hydrogen concentration in the reactor was 90 mole percent. The results obtained in these two parallel runs are shown in Table V below.

TABLE V

EFFECT OF ADDED HYDROGEN UPON CONVERSION OF NORMAL PARAFFINS

| Run | A | B |
|---|---|---|
| Contacting temp., °F | 850 | 850 |
| Contacting pressure, mm. Hg | 750 | 750 |
| Feed rate, W./W./Hr | 0.1 | 0.1 |
| $H_2$ conc. in reactor, mole percent | 0 | 90 |
| 0° F. pour point product, g./100 g. sieve | 173 | 242 |
| Wt. percent yield on feed | 79 | 84 |
| −30° F. pour point product, g./100 g. sieve * | 123 | 177 |
| Wt. percent yield on feed | 77 | 82 |
| Bromine No. of product | 6.5 | 5.7 |

*Product adjusted to 325° F. initial vapor temperature.

Referring to Table V, it can be seen that the presence of the added hydrogen in Run B resulted in an increase in sieve capacity of about 40 to 45% and an increase in yield, based upon feed, of about 5% over the values obtained in Run A. This improvement is shown with respect to both the 0° and the −30° F. product. The bromine numbers of the two products indicate that the improvement was primarily due to the purging of the gas, rather than hydrogenation of olefins, although some hydrogenation did occur. From this it can be seen that the improvement obtained is not limited to the use of hydrogen and that other gases, nitrogen for example, may be used as purging agents during the contacting step of the process. The improvement due to the use of such a purging agent is a significant one and for this reason it is preferred to employ such an agent.

What is claimed is:

1. An improved process for selectively removing normal paraffin hydrocarbons from a hydrocarbon oil boiling between about 100° and about 750° F. which comprises contacting said oil in vapor phase with a crystalline metallic alumino-silicate having uniform pore spaces of about 5 Angstrom units *in contact* [and concomitantly purging hydrocarbon fragments from the said pores of the crystalline metallic alumino-silicate] with a gas having a molecular diameter less than about 5 Angstrom units at a temperature of from about 800 to about 1000° F. in a contacting zone, said gas selected from the group consisting of hydrogen, nitrogen, carbon dioxide and inert gas, withdrawing oil vapor [containing olefins formed by the selective conversion of normal paraffins] from said zone, continuing said contacting until the vapor withdrawn has an undesirably high normal paraffins content [, and thereafter regenerating said metallic alumino-silicate by contact with an oxygen-containing gas at elevated temperature].

2. A process as defined by claim 1 wherein said oil is contacted with said metallic alumino-silicate at a temperature between 850 and about 1000° F.

3. A process as defined by claim 1 wherein said oil is contacted with said metallic alumino-silicate *and* [with concomitant purging with] nitrogen gas.

4. A process as defined cyaim 1 wherein said *gas is hydrogen* [oil is contacted with said metallic alumino-silicate with concomitant purging with from about 5 to about 95 mole percent of said gas having a molecular diameter less than about 5 Angstrom units].

5. An improved process for selectively converting normal paraffins in a hydrocarbon oil [to olefins] which comprises contacting said oil in vapor phase at a temperature of from about 800 to 1000° F. with a crystalline metallic alumino-silicate having uniform pore spaces of about 5 Angstrom units in a contacting zone [and concomitantly purging hydrocarbon fragments from the said pores of the crystalline metallic alumino-silicate] *in contact* with a gas having a molecular diameter less than about 5 Angstrom units, said gas being selected from the group consisting of hydrogen, nitrogen, carbon dioxide and inert gas, and withdrawing from said zone an oil having a reduced normal paraffins content [and an increased olefins content].

References Cited

The following references, cited by the Examiner, are of record in the patented file of this patent or the original patent.

UNITED STATES PATENTS

| | | | |
|---|---|---|---|
| 3,039,953 | 6/1962 | Eng | 208—26 |
| 3,033,778 | 5/1962 | Frilette | 208—120 |
| 2,935,459 | 5/1960 | Hess et al. | 208—65 |
| 2,952,630 | 9/1960 | Eggertsen et al. | 208—310 |

DELBERT E. GANTZ, Primary Examiner

C. E. SPRESSER, Jr., Assistant Examiner

U.S. Cl. X.R.

208—110, 112, 120, 26; 260—677 R